US011541058B2

(12) United States Patent
Hussey et al.

(10) Patent No.: US 11,541,058 B2
(45) Date of Patent: Jan. 3, 2023

(54) PHARMACEUTICAL AQUEOUS FORMULATION COMPRISING 1-(4-{[4-(DIMETHYLAMINO)PIPERIDIN-1-YL]CARBONYL}PHENYL)-3-[4-(4,6-DIMORPHOLIN-4-YL-1,3,5-TRIAZIN-2-YL)PHENYL] UREA

(71) Applicant: PFIZER INC., New York, NY (US)

(72) Inventors: James Joseph Hussey, Sandwich (GB); Andrew Gilbert Bright, Winchester (GB)

(73) Assignee: PFIZER INC., New York, NY (US)

( * ) Notice: Subject to any disclaimer, the term of this patent is extended or adjusted under 35 U.S.C. 154(b) by 41 days.

(21) Appl. No.: 16/641,045

(22) PCT Filed: Aug. 20, 2018

(86) PCT No.: PCT/IB2018/056281
§ 371 (c)(1),
(2) Date: Feb. 21, 2020

(87) PCT Pub. No.: WO2019/038657
PCT Pub. Date: Feb. 28, 2019

(65) Prior Publication Data
US 2021/0267988 A1    Sep. 2, 2021

Related U.S. Application Data

(60) Provisional application No. 62/703,022, filed on Jul. 25, 2018, provisional application No. 62/681,720, filed on Jun. 7, 2018, provisional application No. 62/550,007, filed on Aug. 25, 2017.

(51) Int. Cl.
| | | |
|---|---|---|
| *A61K 31/5377* | (2006.01) | |
| *A61K 9/08* | (2006.01) | |
| *A61K 9/19* | (2006.01) | |
| *A61K 47/40* | (2006.01) | |
| *A61K 47/20* | (2006.01) | |
| *A61K 9/00* | (2006.01) | |
| *A61K 47/26* | (2006.01) | |

(52) U.S. Cl.
CPC ........ *A61K 31/5377* (2013.01); *A61K 9/0019* (2013.01); *A61K 9/08* (2013.01); *A61K 9/19* (2013.01); *A61K 47/20* (2013.01); *A61K 47/26* (2013.01); *A61K 47/40* (2013.01)

(58) Field of Classification Search
CPC .... A61K 31/5377; A61K 9/0019; A61K 9/08; A61K 9/19; A61K 47/20; A61K 47/26; A61K 47/40
USPC ...................................................... 514/232.2
See application file for complete search history.

(56) References Cited

U.S. PATENT DOCUMENTS

| | | | |
|---|---|---|---|
| 8,039,469 B2 | 10/2011 | Venkatesan et al. | |
| 8,217,036 B2 | 7/2012 | Venkatesan et al. | |
| 8,445,486 B2 | 5/2013 | Venkatesan et al. | |
| 8,575,159 B2 | 11/2013 | Venkatesan et al. | |
| 8,748,421 B2 | 6/2014 | Venkatesan | |
| 8,859,542 B2 | 10/2014 | Venkatesan | |
| 9,174,963 B2 | 11/2015 | Venkatesan et al. | |
| 9,895,378 B2 | 2/2018 | Bagrodia et al. | |
| 10,022,381 B2 | 7/2018 | Venkatesan et al. | |
| 10,071,100 B2 | 9/2018 | Bagrodia et al. | |
| 10,172,942 B2 | 1/2019 | Back et al. | |
| 10,660,959 B2 | 5/2020 | Back et al. | |
| 2009/0291079 A1 | 11/2009 | Venkatesan et al. | |
| 2011/0312955 A1 | 12/2011 | Venkatesan et al. | |
| 2013/0005723 A1 | 1/2013 | Venkatesan et al. | |
| 2013/0109670 A1 | 5/2013 | Venkatesan et al. | |
| 2013/0315865 A1 | 11/2013 | Venkatesan et al. | |
| 2014/0220112 A1 | 8/2014 | Szoka, Jr. et al. | |
| 2014/0248239 A1 | 9/2014 | Venkatesan et al. | |
| 2015/0011752 A1 | 1/2015 | Venkatesan et al. | |
| 2015/0258102 A1 | 9/2015 | Bagrodia et al. | |
| 2017/0119778 A1 | 5/2017 | Venkatesan et al. | |
| 2017/0360935 A1 | 12/2017 | Back et al. | |
| 2018/0125854 A1 | 5/2018 | Bagrodia et al. | |
| 2019/0105390 A1 | 4/2019 | Back et al. | |
| 2021/0177857 A1 | 6/2021 | Bagrodia et al. | |
| 2021/0212944 A1 | 7/2021 | Hussey et al. | |

FOREIGN PATENT DOCUMENTS

| | | | |
|---|---|---|---|
| JP | 2002-532438 A | 10/2002 | |
| JP | 2005-521670 A | 7/2005 | |
| JP | 2010-215620 A | 9/2010 | |
| WO | 2009/143313 A1 | 11/2009 | |
| WO | 2010/096619 A1 | 8/2010 | |
| WO | 2016/097949 A1 | 6/2016 | |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
U.S. Appl. No. 14/927,763, filed Oct. 30, 2015, Aranapakam Mudumbai Venkatesan.
U.S. Appl. No. 14/477,650, filed Sep. 4, 2014, Aranapakam Mudumbai Venkatesan.

(Continued)

*Primary Examiner* — Kristin A Vajda
(74) *Attorney, Agent, or Firm* — Nelson Mullins Riley & Scarborough LLP; Jane E. Remillard, Esq.

(57) ABSTRACT

The present invention relates to a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a pharmaceutically acceptable alkanesulphonate salt thereof, that is a clear solution. Such a formulation is particularly suitable for intravenous or parenteral administration to a patient.

30 Claims, 3 Drawing Sheets

(56) References Cited

OTHER PUBLICATIONS

Figure 1:
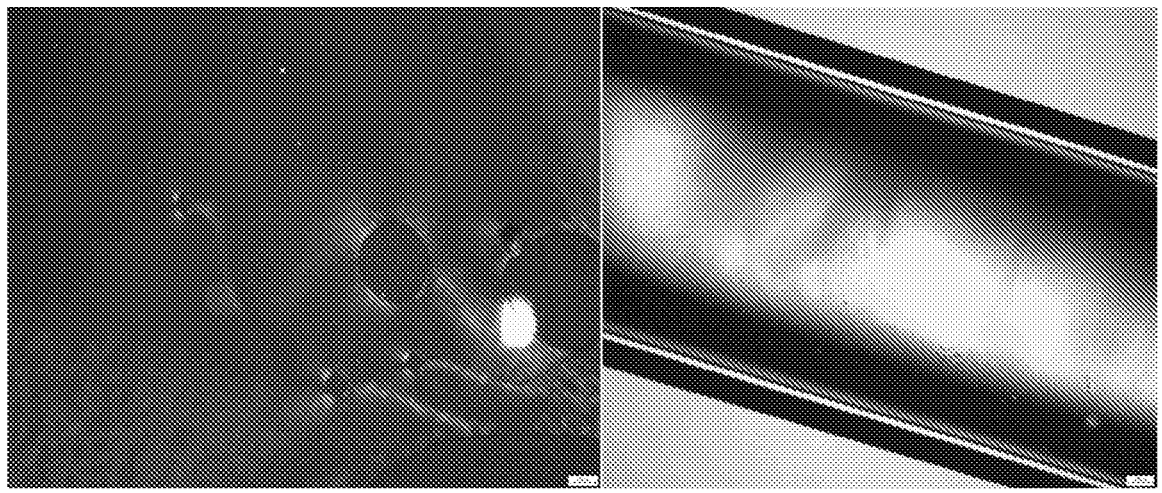

U.S. Appl. No. 14/259,414, filed Apr. 23, 2014, Aranapakam Mudumbai Venkatesan.
U.S. Appl. No. 13/950,584, filed Jul. 25, 2013, Aranapakam Mudumbai Venkatesan.
U.S. Appl. No. 13/718,928, filed Dec. 18, 2012, Aranapakam Mudumbai Venkatesan.
U.S. Appl. No. 13/490,309, filed Jun. 6, 2012, Aranapakam Mudumbai Venkatesan.
U.S. Appl. No. 13/218,571, filed Aug. 26, 2011, Aranapakam Mudumbai Venkatesan.
U.S. Appl. No. 12/470,521, filed May 22, 2009, Aranapakam Mudumbai Venkatesan.
U.S. Appl. No. 16/189,009, filed Nov. 13, 2018, Kevin Richard Back.
U.S. Appl. No. 15/534,999, filed Jun. 9, 2017, Kevin Richard Back.
U.S. Appl. No. 14/656,899, filed Mar. 13, 2015, Shubha Bagrodia.
U.S. Appl. No. 15/860,881, filed Jan. 3, 2018, Shubha Bagrodia.
U.S. Appl. No. 17/183,596, filed Feb. 24, 2021, Shubha Bagrodia.
U.S. Appl. No. 15/734,147, filed Dec. 1, 2020, James Joseph Hussey.
Venkatesan et al., "Bis(morpholino-1,3,5-triazine) Derivatives: Potent Adenosine 5'-Triphosphate Competitive Phosphatidylinositol-3-kinease/Mammalian Target of Rapamycin Inhibitors: Discovery of Compound 26 (PKI-587), a Highly Efficacious Dual Inhibitor", Journal Medicinal Chemistry, 2010, 53, 2636-2645.
Singh, Jai, Optical Properties of Condensed Matter and Applications:, Wiley, Oct. 2006.
International Search Report dated Nov. 29, 2018 for International application No. PCT/IB2018/056281, filed Aug. 20, 2018.
Written Opinion of the International Searching Authority for International application No. PCT/IB2018/056281, filed Aug. 20, 2018.
ClinicalTrials.gov Identifier: NCT00940498, "Study of PF-05212384 (Also Known as PKI-587)Administered Intravenously To Subjects With Solid Tumors (B2151001)," Nov. 2, 2018, 41 pages.
ClinicalTrials.gov Identifier: NCT01420081, "A Study Of Two Dual PI3K/mTOR Inhibitors, PF-04691502 And PF-05212384 In Patients With Recurrent Endometrial Cancer," Jan. 8, 2019, 33 pages.
ClinicalTrials.gov Identifier: NCT01920061, "A Study Of PF-05212384 In Combination With Other Anti-Tumor Agents and in Combination With Cisplatin in Patients With Triple Negative Breast Cancer in an Expansion Arm (TNBC)," Oct. 7, 2021, 87 pages.
Wainberg et al., "Phase I Study of the PI3K/mTOR Inhibitor Gedatolisib (PF-05212384) in Combination with Docetaxel, Cisplatin, and Dacomitinib," J. Clin. Oncol. 34(15 suppl): 2566, 1 pages (2016).
Shapiro, G. et al., "First-in-Human Study of PF-05212384 (PKI-587), a Small-Molecule, Intravenous, Dual Inhibitor of PI3K and mTOR in Patients with Advanced Cancer," Cancer Therapy: Clinical Cancer Research, vol. 21(8): 18 pages (2015).
Layman et al., "Phase Ib Expansion Study of Gedatolisib in Combination with Palbociclib and Endocrine Therapy in Women with ER+ Advanced Breast Cancer," San Antonio Breast Cancer Symposium Poster, Dec. 2021, 1 page.
Lindblad, O. et al., "Aberrant activation of the PI3K/mTOR pathway promotes resistance to sorafenib in AML," Ooncogene, vol. 35(39):5119-5131 (2016).
Venkatesan et al., "Bis(morpholino-1,3,5-triazine) derivatives: potent adenosine 5'-triphosphate competitive phosphatidylinositol-3-kinase/ mammalian target of rapamycin inhibitors: discovery of compound 26 (PKI-587), a highly efficacious dualinhibitor," Journal of Medicinal Chemistry, vol. 53(6)2636-2645 (2010).

* cited by examiner

OPM micrographs of Example 5B containing 22mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea in 100mM ESA

- Left image – Formulation showing liquid crystal phase under glass slide and cover slip
- Right image – Formulation showing liquid crystal phase in a capillary tube.

OPM micrographs of Example 5A containing 22mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea in 100mM MSA

- Left image – Formulation under glass slide and cover slip
- Right image – Formulation in a capillary tube.

re. European Pharmacopoeia Method 2.9.20: *"Figure 2.9.20.-1. – Apparatus for visible particles"*

PHARMACEUTICAL AQUEOUS FORMULATION COMPRISING 1-(4-{[4-(DIMETHYLAMINO)PIPERIDIN-1-YL]CARBONYL}PHENYL)-3-[4-(4,6-DIMORPHOLIN-4-YL-1,3,5-TRIAZIN-2-YL)PHENYL] UREA

CROSS-REFERENCE TO RELATED APPLICATIONS

This Application is the national stage filing under 35 U.S.C. 371 of Patent Cooperation Treaty Patent Application No. PCT/IB2018/056281, filed Aug. 20, 2018, which claims the benefit of priority from U.S. Provisional Application No. 62/550,007 filed Aug. 25, 2017, U.S. Provisional Application No. 62/681,720 filed Jun. 7, 2018 and U.S. Provisional Application No. 62/703,022 filed Jul. 25, 2018, the contents of each of which are hereby incorporated by reference in their entirety.

The present invention relates to a pharmaceutical formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a pharmaceutically acceptable alkanesulphonate salt thereof. More specifically, the present invention relates to a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a pharmaceutically acceptable alkanesulphonate salt thereof, that is a clear solution. Such a formulation is particularly suitable for intravenous or parenteral administration to a patient.

1-(4-{[4-(Dimethylamino)piperidin-1-yl]carbonyl}phenyl)-3-[4-(4,6-dimorpholin-4-yl-1,3,5-triazin-2-yl)phenyl]urea, and preparations thereof, are disclosed in WO2009/143313. The compound is an inhibitor of PI3 kinase and mTOR that is useful for the treatment of cancer.

A crystalline form of 1-(4-{[4-(dimethylamino)piperidin-1-yl]carbonyl}phenyl)-3-[4-(4,6-dimorpholin-4-yl-1,3,5-triazin-2-yl)phenyl]urea, and process for the preparation thereof, are disclosed in WO2010/096619.

WO2016/097949 describes a pharmaceutical aqueous solution formulation suitable for intravenous administration comprising (i) 1-(4-{[4-(dimethylamino)piperidin-1-yl]carbonyl}phenyl)-3-[4-(4,6-dimorpholin-4-yl-1,3,5-triazin-2-yl)phenyl]urea, or a lactate salt thereof, lactic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 6 mg/ml and sufficient lactic acid is present to provide a clear solution; or (ii) 1-(4-{[4-(dimethylamino)piperidin-1-yl]carbonyl}phenyl)-3-[4-(4,6-dimorpholin-4-yl-1,3,5-triazin-2-yl)phenyl]urea, or a phosphate salt thereof, orthophosphoric acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 4 mg/ml and sufficient orthophosphoric acid is present to provide a clear solution. Lyophilisation of such formulations are also described. Of the many acids tested (i.e. citric acid, succinic acid, acetic acid, glycine, tartaric acid, maleic acid, malic acid, hydrochloric acid, lactic acid and orthophosphoric acid), only lactic acid and orthophosphoric acid are found to be capable of achieving a clear solution with a concentration of 1-(4-{[4-(dimethylamino)piperidin-1-yl]carbonyl}phenyl)-3-[4-(4,6-dimorpholin-4-yl-1,3,5-triazin-2-yl)phenyl]urea of 3 mg/ml or above.

1-(4-{[4-(Dimethylamino)piperidin-1-yl]carbonyl}phenyl)-3-[4-(4,6-dimorpholin-4-yl-1,3,5-triazin-2-yl)phenyl]urea, also known as gedatolisib, has the chemical structure:

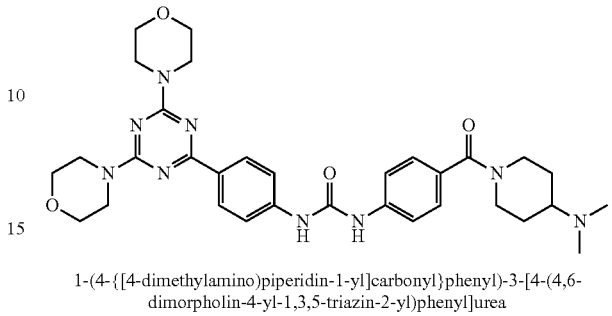

1-(4-{[4-dimethylamino)piperidin-1-yl]carbonyl}phenyl)-3-[4-(4,6-dimorpholin-4-yl-1,3,5-triazin-2-yl)phenyl]urea 1-(4-{[4-(Dimethylamino)piperidin-1-yl]carbonyl}phenyl)-3-[4-(4,6-dimorpholin-4-yl-1,3,5-triazin-2-yl)phenyl]urea may be prepared in crystalline form and is chemically and physically stable at 25° C. and 60% Relative Humidity (RH) for up to 3 years in this form. However, this free base is insufficiently water soluble to allow the preparation of an aqueous solution formulation suitable for intravenous or parenteral administration at the therapeutic dosage levels required.

There is a need to develop a pharmaceutically acceptable aqueous solution formulation of 1-(4-{[4-(dimethylamino)piperidin-1-yl]carbonyl}phenyl)-3-[4-(4,6-dimorpholin-4-yl-1,3,5-triazin-2-yl)phenyl]urea that is (a) chemically stable on storage (e.g. at 25° C. and 60% RH), (b) that will facilitate effective intravenous (or parenteral) administration of the drug to a mammal, including a human being, and (c), preferably, to achieve a solution concentration of 1-(4-{[4-(dimethylamino)piperidin-1-yl]carbonyl}phenyl)-3-[4-(4,6-dimorpholin-4-yl-1,3,5-triazin-2-yl)phenyl]urea that is at least 6 mg/ml.

A solution concentration of 1-(4-{[4-(dimethylamino)piperidin-1-yl]carbonyl}phenyl)-3-[4-(4,6-dimorpholin-4-yl-1,3,5-triazin-2-yl)phenyl]urea that is at least 6 mg/ml is desirable to allow dose administration to subjects using a single vial presentation of the commercial drug product. A lyophilised drug product (for reconstitution) containing less than 6 mg/ml drug product solution will require multiple vials to deliver the required therapeutic dose. A multiple vial approach to dose delivery is not desirable given current regulatory expectations for these product types.

Preferably, the formulation is suitable for intravenous or parenteral administration of 1-(4-{[4-(dimethylamino)piperidin-1-yl]carbonyl}phenyl)-3-[4-(4,6-dimorpholin-4-yl-1,3,5-triazin-2-yl)phenyl]urea in view of the particular pharmacokinetic and bioavailability characteristics of this drug.

It is essential that an intravenous formulation of any drug is a solution to facilitate safe and effective administration to a patient. It must be particle-free, and not form a gel or suspension. A clear, aqueous solution is preferred.

A "clear solution" is defined herein as a visually clear solution, which may bear a solution opalescence, that is essentially free from any visible particulates that can be observed on a visual inspection. Generally, if any particulate matter is observed, the formulation is not suitable for intravenous administration and should not be utilised as occlusion of blood vessels may occur. Accordingly, in view of the qualitative nature of the visual test, the term "essentially free from any visible particulates" is usually applied when no visible particulate matter is observed.

Particulate matter may be defined as follows:
speck—discrete particle whose shape cannot be determined without magnification
smoke or swirl—fine particles that look like smoke or a tornado and usually originate from the sample vial floor and twist upward as the vial is swirled
flocculent material—loosely aggregated particles or soft flakes
particulates with a definite shape or characteristic can be described as glass-like, metallic-looking, etc.

The visual inspection can be conducted in accordance with the method defined in European Pharmacopoeia Method 2.9.20 entitled "Particulate contamination: visible particles". This method determines particulate contamination of injections and infusions by extraneous, mobile, undissolved particles, other than gas bubbles, that may be present in the solutions. The test is intended to provide a simple procedure for the visual assessment of the quality of parenteral solutions as regards visible particles.

In European Pharmacopoeia Method 2.9.20 the apparatus (see "FIG. 2.9.20.-i" shown in FIG. 3) consists of a viewing station comprising:

a matt black panel of appropriate size held in a vertical position
a non-glare white panel of appropriate size held in a vertical position next to the black panel
an adjustable lampholder fitted with a suitable, shaded, white-light source and with a suitable light diffuser (a viewing illuminator containing two 13 Watt fluorescent tubes, each 525 mm in length, is suitable). The intensity of illumination at the viewing point is maintained between 2000 lux and 3750 lux, although higher values are preferable for coloured glass and plastic containers.

The Method states: "Remove any adherent labels from the container and wash and dry the outside. Gently swirl or invert the container, ensuring that air bubbles are not introduced, and observe for about 5 seconds in front of the white panel. Repeat the procedure in front of the black panel. Record the presence of any particles." A suitable method in accordance with European Pharmacopoeia Method 2.9.20 that has been used for the present invention is described in Example 1(i).

Other validated methods may be also be used for the dermination of if any visible particulates are present. Such methods include Optical Polarised Microscopy ("OPM"). A suitable OPM method that has been used for the present invention is described in Example 1(ii).

The present invention relates to a pharmaceutical aqueous formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, or a methanesulphonate or ethanesulphonate salt thereof, methanesulphonic acid or ethanesulphonic acid, and, optionally, a pharmaceutically acceptable beta- or gamma-cyclodextrin, that is a clear solution (hereafter "the formulation of the invention").

Preferably, methanesulphonic acid (and methanesulphonate salts) are used in the formulations of the invention.

In an embodiment of the invention is provided a pharmaceutical aqueous solution formulation comprising (a) 1-(4-{[4-(dimethylamino)piperidin-1-yl]carbonyl}phenyl)-3-[4-(4,6-dimorpholin-4-yl-1,3,5-triazin-2-yl)phenyl]urea, or a methanesulphonate salt thereof, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 35 mg/ml or up to 30 mg/ml and sufficient methanesulphonic acid is present to provide a clear solution; or (b) 1-(4-{[4-(dimethylamino)piperidin-1-yl]carbonyl}phenyl)-3-[4-(4,6-dimorpholin-4-yl-1,3,5-triazin-2-yl)phenyl]urea, or an ethanesulphonate salt thereof, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 35 mg/ml or up to 30 mg/ml and sufficient ethanesulphonic acid is present to provide a clear solution.

In an embodiment of the invention is provided a pharmaceutical aqueous solution formulation comprising (a) 1-(4-{[4-(dimethylamino)piperidin-1-yl]carbonyl}phenyl)-3-[4-(4,6-dimorpholin-4-yl-1,3,5-triazin-2-yl)phenyl]urea, or a methanesulphonate salt thereof, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml and sufficient methanesulphonic acid is present to provide a clear solution; or (b) 1-(4-{[4-(dimethylamino)piperidin-1-yl]carbonyl}phenyl)-3-[4-(4,6-dimorpholin-4-yl-1,3,5-triazin-2-yl)phenyl]urea, or an ethanesulphonate salt thereof, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml and sufficient ethanesulphonic acid is present to provide a clear solution.

The "solution concentration" values referred to herein relate to the concentration of the free base of 1-(4-{[4-(dimethylamino)piperidin-1-yl]carbonyl}phenyl)-3-[4-(4,6-dimorpholin-4-yl-1,3,5-triazin-2-yl)phenyl]urea in the formulation of the invention.

It has been found that the use of methanesulphonic acid and ethanesulphonic acid enables a solution concentration of up to 30 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea to be achieved for a pharmaceutical aqueous solution formulation that is suitable for intravenous or parenteral administration to a patient, i.e. a clear, essentially particle-free solution. Such formulations may have an opalescent hue but they are still essentially particle-free.

Without being bound by theory, the opalescent hue may be caused by chromonic liquid crystal formation. Chromonic liquid crystals are formed by the formation of pi-pi stacked aromatic sections of a molecule forming column like stacks of dimers, trimers and low molecular weight oligomers of the molecules. The stacks that form can be shown via OPM to be non-crystalline microstructures associated to a chromonic liquid crystal. The non-crystalline microstructures exhibit interactions that are not permanent and there is movement to maintain the system in a free energy equilibrium. The opalescence of the solution comes from the alteration of the refractive index of the solution due to the formation of these stacks. OPM micrographs of the solutions will show that there is no crystalline material present and instead there is a chromonic liquid crystal phase. The presence of a liquid crystal phase results in a solution with opacity and/or opalescence due to a difference in refractive index within the solution formed. For a discussion on liquid crystal formation see "Optical Properties of Condensed Matter and Applications", Jai Singh (Editor), ISBN: 978-0-470-02193-4, Wiley, October 2006.

Such a formulation can be directly administered to the patient (in order to avoid degradation occurring), intravenously or parenterally, preferably with the addition of a tonicity modifier. Alternatively, for administration to a patient at a later date, such a formulation, optionally containing a bulking agent and/or tonicity modifier, may be first freeze-dried to prepare a lyophilised solid composition that is chemically stable on storage for preferably at least 2 years, and which lyophilised solid composition then can be constituted, or reconstituted, to provide a clear aqueous solution, preferably with the addition of a tonicity modifier, as necessary, immediately prior to administration to a patient by the intravenous (or parenteral) route. The reconstituted or constituted solution may be added to an infusion bag prior to administration to a patient.

In respect of the formulations comprising methanesulphonic acid, it has been found that above a solution concentration of 1-(4-{[4-(dimethylamino)piperidin-1-yl]carbonyl}phenyl)-3-[4-(4,6-dimorpholin-4-yl-1,3,5-triazin-2-yl)phenyl]urea of 35 mg/ml or above, the necessary clear solutions at the pH required for intravenous administration to a patient are not obtained, or are not obtained consistently.

In respect of the formulations comprising ethanesulphonic acid, it has been found that above a solution concentration of 1-(4-{[4-(dimethylamino)piperidin-1-yl]carbonyl}phenyl)-3-[4-(4,6-dimorpholin-4-yl-1,3,5-triazin-2-yl)phenyl]urea of above 35 mg/ml or above, the necessary clear solutions at the pH required for intravenous administration to a patient are not obtained, or are not obtained consistently.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 35 mg/ml or up to 30 mg/ml and sufficient methanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 35 mg/ml or up to 30 mg/ml and sufficient methanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml and sufficient methanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml and sufficient methanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 22 mg/ml and sufficient methanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 22 mg/ml and sufficient methanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 8 to 30 mg/ml, from 10 to 30 mg/ml, from 8 to 22 mg/ml, from 10 to 22 mg/ml, from 15 to 22 mg/ml, from 6 to 25 mg/ml or from 10 to 25 mg/ml, and sufficient methanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 8 to 30 mg/ml, from 10 to 30 mg/ml, from 8 to 22 mg/ml, from 10 to 22 mg/ml, from 15 to 22 mg/ml, from 6 to 25 mg/ml or from 10 to 25 mg/ml, and sufficient methanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 35 mg/ml or up to 30 mg/ml and sufficient ethanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 35 mg/ml or up to 30 mg/ml and sufficient ethanesulphonic acid is present to provide a clear solution.

One embodiment of the formulation of the invention provides a pharmaceutical aqueous solution formulation comprising 1-(4-{[4-(dimethylamino)piperidin-1-yl]

carbonyl}phenyl)-3-[4-(4,6-dimorpholin-4-yl-1,3,5-triazin-2-yl)phenyl]urea, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml and sufficient ethanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml and sufficient ethanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 22 mg/ml and sufficient ethanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 22 mg/ml and sufficient ethanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 8 to 30 mg/ml, from 10 to 30 mg/ml, from 8 to 22 mg/ml, from 10 to 22 mg/ml, from 15 to 22 mg/ml, from 6 to 25 mg/ml or from 10 to 25 mg/ml, and sufficient ethanesulphonic acid is present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 8 to 30 mg/ml, from 10 to 30 mg/ml, from 8 to 22 mg/ml, from 10 to 22 mg/ml, from 15 to 22 mg/ml, from 6 to 25 mg/ml or from 10 to 25 mg/ml, and sufficient ethanesulphonic acid is present to provide a clear solution.

A further embodiment of the formulation of the invention may optionally additionally comprise a pharmaceutically acceptable beta- or gamma-cyclodextrin. Examples of such a pharmaceutically acceptable beta-cyclodextrin are 2-hydroxypropyl-beta-cyclodextrin and sulphobutylether-3-cyclodextrin (SBECD). Examples of such a pharmaceutically acceptable gamma-cyclodextrin are gamma-cyclodextrin and 2-hydroxypropyl-gamma-cyclodextrin. Preferably, hydroxypropyl-beta-cyclodextrin is used in the formulations of the invention. By use of a pharmaceutically acceptable beta- or gamma-cyclodextrin it has been found that clear solutions may be achieved with no opalescence and/or containing higher concentrations of 1-(4-{[4-(dimethylamino)piperidin-1-yl]carbonyl}phenyl)-3-[4-(4,6-dimorpholin-4-yl-1,3,5-triazin-2-yl)phenyl]urea.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, methanesulphonic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 55 mg/ml or up to 50 mg/ml and sufficient methanesulphonic acid and 2-hydroxypropyl-beta-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate, methanesulphonic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 55 mg/ml or up to 50 mg/ml and sufficient methanesulphonic acid and 2-hydroxypropyl-beta-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, methanesulphonic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of up to 45 mg/ml, up to 40 mg/ml, up to 35 mg/ml, up to 30 mg/ml, from 6 to 50 mg/ml, from 6 to 30 mg/ml, from 8 to 30 mg/ml, from 10 to 35 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient methanesulphonic acid and 2-hydroxypropyl-beta-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate, methanesulphonic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of up to 45 mg/ml, up to 40 mg/ml, up to 35 mg/ml, up to 30 mg/ml, from 6 to 50 mg/ml, from 6 to 30 mg/ml, from 8 to 30 mg/ml, from 10 to 35 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient methanesulphonic acid and 2-hydroxypropyl-beta-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, methanesulphonic acid, sulphobutylether-3-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 35 mg/ml or up to 30 mg/ml and sufficient methanesulphonic acid and sulphobutylether-β-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate, methanesulphonic acid, sulphobutylether-3-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 35 mg/ml or up to 30 mg/ml and sufficient methanesulphonic acid and sulphobutylether-3-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, methanesulphonic acid, sulphobutylether-3-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml, from 8 to 30 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient methanesulphonic acid and sulphobutylether-3-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate, methanesulphonic acid, sulphobutylether-3-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml, from 8 to 30 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient methanesulphonic acid and sulphobutylether-β-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, methanesulphonic acid, gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 35 mg/ml or up to 30 mg/ml and sufficient methanesulphonic acid and gamma-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate, methanesulphonic acid, gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 35 mg/ml or up to 30 mg/ml and sufficient methanesulphonic acid and gamma-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, methanesulphonic acid, gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from from 6 to 30 mg/ml, from 8 to 30 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient methanesulphonic acid and gamma-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate, methanesulphonic acid, gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml, from 8 to 30 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient methanesulphonic acid and gamma-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulphonic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 40 mg/ml or up to 35 mg/ml and sufficient ethanesulphonic acid and 2-hydroxypropyl-beta-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 40 mg/ml or up to 35 mg/ml and sufficient ethanesulphonic acid and 2-hydroxypropyl-beta-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulphonic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of up to 30 mg/ml, from 6 to 30 mg/ml, from 8 to 30 mg/ml, from 10 to 35 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient ethanesulphonic acid and 2-hydroxypropyl-beta-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of up to 30 mg/ml, from 6 to 30 mg/ml, from 8 to 30 mg/ml, from 10 to 35 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient ethanesulphonic acid and 2-hydroxypropyl-beta-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulphonic acid, sulphobutylether-3-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 40 mg/ml or up to 35 mg/ml and sufficient ethanesulphonic acid and sulphobutylether-β-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid, sulphobutylether-3-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 40 mg/ml or up to 35 mg/ml and sufficient ethanesulphonic acid and sulphobutylether-3-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulphonic acid, sulphobutylether-3-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of up to 30 mg/ml, from 6 to 30 mg/ml, from 8 to 30 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient ethanesulphonic acid and sulphobutylether-3-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid, sulphobutylether-3-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of up to 30 mg/ml, from 6 to 30 mg/ml, from 8 to 30 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient ethanesulphonic acid and sulphobutylether-β-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulphonic acid, gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 25 mg/ml or up to 20 mg/ml and sufficient ethanesulphonic acid and gamma-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid, gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 25 mg/ml or up to 20 mg/ml and sufficient methanesulphonic acid and gamma-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulphonic acid, gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 20 mg/ml, from 8 to 20 mg/ml, from 10 to 20 mg/ml, from 8 to 15 mg/ml, or from 15 to 20 mg/ml and sufficient ethanesulphonic acid and gamma-cyclodextrin are present to provide a clear solution.

One embodiment of the formulation of the invention provides a pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid, gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 20 mg/ml, from 8 to 20 mg/ml, from 10 to 20 mg/ml, from 8 to 15 mg/ml, or from 15 to 20 mg/ml and sufficient ethanesulphonic acid and gamma-cyclodextrin are present to provide a clear solution.

The preferred concentration of methanesulphonic acid or ethanesulphonic acid for use in a formulation of the invention is from 10 to 200 mM, 20 to 200 mM, 30 to 200 mM or from 50 to 200 mM, and preferably is about 50 mM, about 100 mM or about 150 mM. Preferably, the concentration of methanesulphonic acid or ethanesulphonic acid is about 100 mM. Preferably, about a 100 mM concentration of methanesulphonic acid is used.

The preferred amount of pharmaceutically acceptable beta- or gamma-cyclodextrin for use in a formulation of the invention is from 2 to 30% w/v, 3 to 20% w/v, from 5 to 20% w/v or from 15 to 30% w/v, and preferably is about 20% w/v or 25% w/v. Preferably, the amount of pharmaceutically acceptable beta- or gamma-cyclodextrin for use in a formulation of the invention is about 20% w/v.

If the formulation of the invention is to be freeze-dried to provide a lyophilised solid composition, a bulking agent may be added to the formulation prior to the freeze-drying process commencing. A bulking agent may not be present if the formulation of the invention contains a pharmaceutically acceptable beta- or gamma-cyclodextrin. The primary function of the bulking agent is to provide the freeze-dried solid with a non-collapsible, structural integrity that will allow rapid reconstitution on constitution of the aqueous formulation prior to administration, and it should also facilitate efficient lyophilisation. Bulking agents are typically used when the total mass of solutes in the formulation is less than 2 g/100 ml. Bulking agents may also be added to achieve isotonicity with blood. The bulking agent may be selected from a saccharide, sugar alcohol, amino acid or polymer, or be a mixture of two or more of any thereof. Preferably, the bulking agent is a sugar or sugar alcohol, or a mixture thereof. Preferably, the sugar is sucrose. Preferably, the sugar alcohol is mannitol.

Preferably, from 5 to 10% w/v of a bulking agent is used, if present.

Reconstitution of the lyophilised solid composition may be achieved by addition of the requisite quantity of water that was present prior to lyophilisation in order that a clear solution is obtained. A tonicity modifier may then be added prior to use.

Constitution of the lyophilised solid composition may be achieved using an appropriate quantity of water and/or an aqueous solution of a suitable tonicity modifier in order to ensure that a clear solution is obtained.

A tonicity modifier may be present prior to intravenous or parenteral administration of the formulation to a patient by injection to avoid crenation or hemolysis of red blood cells, and to mitigate or avoid pain and discomfort to the patient. This requires that the formulation to be administered to the patient has an effective osmotic pressure that is approximately the same as that of the blood of the patient.

Suitable tonicity modifiers are non-ionic tonicity modifiers such as glycerol, sorbitol, mannitol, sucrose, propylene glycol or dextrose, or a mixture of any 2 or more thereof. Preferably the non-ionic tonicity modifier is dextrose, sucrose or mannitol, or is a mixture of any 2 or more thereof.

Preferably, from 1 to 5% w/v of a tonicity modifier is used.

Aqueous pharmaceutical formulations of the invention that are suitable for intravenous administration generally have a pH of from 3 to 9. However, lower pH values are tolerated in certain settings. Preferably, the pH is from 3 to 8 or from 4 to 8.

The formulation of the invention may be used for the curative, palliative or prophylactic treatment of cancer in a mammal, including a human being. The cancer to be treated may be selected from the group consisting of leukemia, skin cancer, bladder cancer, breast cancer, uterus cancer, ovary cancer, prostate cancer, lung cancer, colon cancer, pancreas cancer, renal cancer, gastric cancer and brain cancer.

The weekly dose of 1-(4-{[4-(dimethylamino)piperidin-1-yl]carbonyl}phenyl)-3-[4-(4,6-dimorpholin-4-yl-1,3,5-triazin-2-yl)phenyl]urea to be administered by the intravenous route for the treatment of cancer using the formulations disclosed herein is preferably in the range of from 100 to 400 mg per week.

The following Figures illustrate the claimed invention:

FIG. 1: OPM micrographs of Example 5B containing 22 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea in 100 mM ESA FIG. 2: OPM micrographs of Example 5A containing 22 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea in 100 mM MSA FIG. 3: re. European Pharmacopoeia Method 2.9.20: "FIG. 2.9.20.-1.—Apparatus for visible particles"

The following Examples describe the preparation of the formulations of the invention.

EXAMPLE 1

Preparation of a Pharmaceutical Aqueous Solution Formulation Comprising 22 mg/ml of 1-(4-{[4-(dimethylamino)piperidin-1-yl]carbonyl}phenyl)-3-[4-(4,6-dimorpholin-4-yl-1,3,5-triazin-2-yl)phenyl] urea and methanesulfonic acid Methanesulfonic acid (99% w/w purity) (0.65 ml) was dissolved in water for irrigation (80 ml). 1-(4-{[4-(Dimethylamino)piperidin-1-yl]carbonyl}phenyl)-3-[4-(4,6-dimorpholin-4-yl-1,3,5-triazin-2-yl)phenyl]urea (220 mg) was added to the solution and stirred until a particle-free solution was achieved. Water for irrigation was added with stirring to achieve a target volume of 100 ml.

(i) Visual Analysis

A sample of the formulation was analysed in accordance with the visual method defined in European Pharmacopoeia Method 2.9.20 (using a Verivide (trade mark) light cabinet and a light meter reading of 3250 lux against a matt black panel and a white panel) to determine if crystallites or particles were present. The sample was tested by this method both when the solution was first made up and then 24 hours thereafter.

(ii) OPM Analysis

A sample of the formulation was placed on a clean glass microscopy slide and covered with a glass cover slip. It was then analysed by OPM using both non-polarised and cross-polarised light under a Nikon LV 100POL (trade mark) microscope with a 10× magnification lens and a 10× magnification eyepiece to determine if crystallites or particles were present. The image was recorded using a DFK 23UP031 TIS USB 3.0 CMOS (trade mark) Colour Industrial Camera 5 MP 1/2,5" and image capture software. The procedure was also repeated using a sample of the formulation in a glass capillary tube. The sample was tested by this method when the solution was first made up, and then at 4 and 24 hours thereafter.

EXAMPLE 2

Preparation of a Pharmaceutical Aqueous Solution Formulation Comprising 22 mg/ml of 1-(4-{[4-(dimethylamino)piperidin-1-yl]carbonyl}phenyl)-3-[4-(4,6-dimorpholin-4-yl-1,3,5-triazin-2-yl)phenyl] urea and ethanesulfonic acid Ethanesulfonic acid (70% w/v) (3144.7 microL), was diluted with water for irrigation (80 ml). 1-(4-{[4-(Dimethylamino)piperidin-1-yl]carbonyl}phenyl)-3-[4-(4,6-dimorpholin-4-yl-1,3,5-triazin-2-yl)phenyl]urea (220 mg) was added to the solution and stirred until a particle-free solution was achieved. Water for irrigation was added with stirring to achieve target volume of 100 ml.

Samples of the formulation were analysed in accordance with the methods of Example 1.

EXAMPLE 3

Preparation of (a) a Pharmaceutical Aqueous Solution Formulation Comprising 22 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea, methanesulfonic acid and mannitol; and (b) a lyophilised composition thereof (a) Methanesulfonic acid (99% w/w purity) (0.65 ml) was dissolved in water for irrigation (80 ml). Mannitol (2.8 g) was dissolved in this buffer solution by stirring to achieve total dissolution. 1-(4-{[4-(Dimethylamino)piperidin-1-yl]carbonyl}phenyl)-3-[4-(4,6-dimorpholin-4-yl-1,3,5-triazin-2-yl)phenyl]urea (220 mg) was added to the solution and stirred until a particle-free solution was achieved. Water for irrigation was added with stirring to achieve a target volume of 100 ml.

Samples of the formulation were analysed in accordance with the methods of Example 1.

(b) The formulation from (a) was filled into 10 mL vials to a target volume of 3 ml. The vials were partially stoppered (not sealed) with a 20 mm Gray Lyo D777-i V10-F597W FluroTec Siliconised (trade mark) stopper. The vials were loaded into stainless steel trays and inserted into a LSL1000 (trade mark) freeze dryer. The shelf temperature was set at 5° C. The freeze drying cycle was run using the tabulated method below.

| Condition | Rate/Hold | Temperature (degrees C.) | Time (min.) | Temperature change (degrees C.) per minute | Pressure |
|---|---|---|---|---|---|
| Loading | Hold | 5 | n/a | n/a | 760 Torr (1 Atmosphere) |
| Stabilisation | Hold | 5 | 120 | n/a | 760 Torr (1 Atmosphere) |
| Freeze | Rate | −40 | 480 | 0.1 deg. C./min | 760 Torr (1 Atmosphere) |
|  | Hold | −40 | 180 | n/a | 760 Torr (1 Atmosphere) |
| Annealing | Rate | −12 | 280 | 0.1 deg. C./min | 760 Torr (1 Atmosphere) |
|  | Hold | −12 | 180 | n/a | 760 Torr (1 Atmosphere) |
| Cooling | Rate | −40 | 280 | 0.1 deg. C./min | 760 Torr (1 Atmosphere) |
| Evacuation | Hold | −40 | 100 | n/a | 90 mTorr |
| Primary Drying | Hold | −40 | 30 | n/a | 90 mTorr |
|  | Rate | −30 | 100 | 0.5 deg. C./min | 90 mTorr |
|  | Hold | −30 | 5450 | n/a | 90 mTorr |
| Secondary Drying | Rate | 20 | 500 | 0.5 deg. C./min | 90 mTorr |
|  | Hold | 20 | 500 | n/a | 90 mTorr |
|  | Rate | 40 | 200 | 0.5 deg. C./min | 90 mTorr |
|  | Hold | 40 | 500 | n/a | 90 mTorr |

The freeze dryer was back-filled with sterile filtered nitrogen to a set point of 500 Torr (ca. 666 mbar or 66,600 Pascals), and the vials were fully closed using the stoppers. The freeze dryer was then vented to atmospheric pressure using sterile filtered air and the vials were unloaded from the freeze dryer.

Each vial contained the freeze dried (lyophilised) formulation as an off-white solid.

EXAMPLE 4

Preparation of (a) a Pharmaceutical Aqueous Solution Formulation Comprising 22 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulfonic acid and mannitol; and (b) a lyophilised Composition Thereof (a) Ethanesulfonic acid (70% w/v) (3144.7 microL), was diluted with water for irrigation (80 ml). Mannitol (2.8 g) was dissolved in the buffer solution and stirred to achieve total dissolution. 1-(4-{[4-(Dimethylamino)piperidin-1-yl]carbonyl}phenyl)-3-[4-(4,6-dimorpholin-4-yl-1,3,5-triazin-2-yl)phenyl]urea (220 mg) was added to the solution and stirred until a particle-free solution was achieved. Water for irrigation was added with stirring to achieve target volume of 100 ml.

Samples of the formulation were analysed in accordance with the methods of Example 1.

(b) The formulation from (a) was filled into 10 mL vials to a target volume of 3 ml. The vials were partially stoppered (not sealed) with a 20 mm Gray Lyo D777-1 V10-F597W FluroTec Siliconised (trade mark) stopper. The vials were loaded into stainless steel trays and inserted into a LSL1000 (trade mark) freeze dryer. The shelf temperature was set at 5° C. The freeze drying cycle was run using the tabulated method below.

| Condition | Rate/Hold | Temperature (degrees C.) | Time (min.) | Temperature change (degrees C.) per minute | Pressure |
|---|---|---|---|---|---|
| Loading | Hold | 5 | n/a | n/a | 760 Torr (1 Atmosphere) |
| Stabilisation | Hold | 5 | 120 | n/a | 760 Torr (1 Atmosphere) |
| Freeze | Rate | −40 | 480 | 0.1 deg. C./min | 760 Torr (1 Atmosphere) |
|  | Hold | −40 | 180 | n/a | 760 Torr (1 Atmosphere) |
| Annealing | Rate | −12 | 280 | 0.1 deg. C./min | 760 Torr (1 Atmosphere) |
|  | Hold | −12 | 180 | n/a | 760 Torr (1 Atmosphere) |
| Cooling | Rate | −40 | 280 | 0.1 deg. C./min | 760 Torr (1 Atmosphere) |
| Evacuation | Hold | −40 | 100 | n/a | 90 mTorr |
| Primary Drying | Hold | −40 | 30 | n/a | 90 mTorr |
|  | Rate | −30 | 100 | 0.5 deg. C./min | 90 mTorr |
|  | Hold | −30 | 5450 | n/a | 90 mTorr |
| Secondary Drying | Rate | 20 | 500 | 0.5 deg. C./min | 90 mTorr |
|  | Hold | 20 | 500 | n/a | 90 mTorr |
|  | Rate | 40 | 200 | 0.5 deg. C./min | 90 mTorr |
|  | Hold | 40 | 500 | n/a | 90 mTorr |

The freeze dryer was back-filled with sterile filtered nitrogen to a set point of 500 Torr (ca. 666 mbar or 66,600 Pascals), and the vials were fully closed using the stoppers. The freeze dryer was then vented to atmospheric pressure using sterile filtered air and the vials were unloaded from the freeze dryer.

Each vial contained the freeze dried (lyophilised) formulation as an off-white solid.

EXAMPLE 5A

Reconstitution of a Pharmaceutical Aqueous Solution Formulation Comprising 22 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea, methanesulfonic acid and mannitol from a lyophilised Solid Composition A vial of lyophilised solid composition prepared in Example 3(b) was reconstituted as follows.

Water for irrigation (3 ml) was injected using a syringe into the vial containing the lyophilised composition prepared in Example 3(b). The mixture was swirled until a particle-free solution was obtained.

The reconstituted formulation was analysed in accordance with the methods of Example 1.

Figure 2:
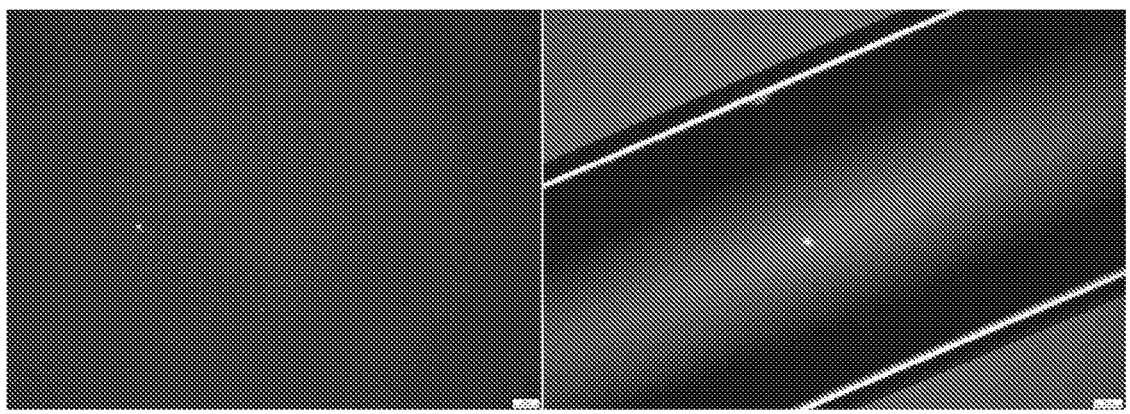

FIG. 2 shows OPM micrographs taken immediately after reconstitution at 100× magnification. There was no evidence of any particulate or crystalline material within the sample.

EXAMPLE 5B

Reconstitution of a Pharmaceutical Aqueous Solution Formulation Comprising 22 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulfonic acid and mannitol from a lyophilised Solid Composition A vial of lyophilised solid composition prepared in Example 4(b) was reconstituted as follows.

Water for irrigation (3 ml) was injected using a syringe into the vial containing the lyophilised composition prepared in Example 4(b). The mixture was swirled until a particle-free solution was obtained.

The reconstituted formulation was analysed in accordance with the methods of Example 1.

FIG. 1 shows OPM micrographs taken immediately after reconstitution at 100× magnification. There is no evidence of any particulate or crystalline material within the sample. The opalescence of the solution that was observed is likely due to the presence of a chromonic liquid crystal phase.

EXAMPLES 6-18

Examples 6-18 were prepared in accordance with the method of the relevant Example 1, 2, 3(a) or 4(a) using the ingredient specification tabulated below.

| Acid | Example | API (mg/ml) | API (mg) | Acid (mM) | Acid (ml) | mannitol (mg) | Target volume (ml) |
|---|---|---|---|---|---|---|---|
| MSA | 1 | 22 | 2200 | 100 | 0.65 | 0 | 100 |
| | 3(a) | 22 | 2200 | 100 | 0.65 | 2800 | 100 |
| | 6 | 8 | 800 | 100 | 0.65 | 4200 | 100 |
| | 7 | 10 | 1000 | 100 | 0.65 | 4000 | 100 |
| | 8 | 13 | 1300 | 100 | 0.65 | 3700 | 100 |
| | 9 | 15 | 1500 | 100 | 0.65 | 3500 | 100 |
| | 10 | 15 | 1500 | 100 | 0.65 | 0 | 100 |
| | 11 | 30 | 3000 | 100 | 0.65 | 2000 | 100 |
| | 12 | 30 | 3000 | 100 | 0.65 | 0 | 100 |
| | 13 | 40 | 4000 | 100 | 0.65 | 1000 | 50 |
| | 14 | 40 | 4000 | 100 | 0.65 | 0 | 50 |
| | 15 | 20 | 2000 | 50 | 0.325 | 3000 | 50 |
| ESA | 2 | 22 | 2200 | 100 | 0.93 | 0 | 100 |
| | 4(a) | 22 | 2200 | 100 | 0.93 | 2800 | 100 |
| | 16 | 30 | 3000 | 100 | 0.93 | 2000 | 100 |
| | 17 | 20 | 2000 | 50 | 0.46 | 3000 | 50 |
| | 18 | 10 | 1000 | 100 | 0.93 | 4000 | 100 |

MSA = methanesulphonic acid
ESA = ethanesulphonic acid
API = 1-(4-{[4-(dimethylamino)piperidin-1-yl]carbonyl}phenyl)-3-[4-(4,6-dimorpholin-4-yl-1,3,5-triazin-2-yl)phenyl]urea

EXAMPLE 19

Preparation of a Pharmaceutical Aqueous Solution Formulation Comprising 35 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea, 20% w/v 2-hydroxypropyl-beta-cyclodextrin and methanesulfonic acid Methanesulfonic acid (99% w/w purity) (0.65 ml, 100 mM) was dissolved in water for irrigation (80 ml). 2-Hydroxypropyl-beta-cyclodextrin (93% w/w adjusted potency) (21.57 g, 14.72 mM) was added and the solution was stirred until a particle-free solution was achieved. 1-(4-{[4-(Dimethylamino)piperidin-1-yl]carbonyl}phenyl)-3-[4-(4,6-dimorpholin-4-yl-1,3,5-triazin-2-yl)phenyl]urea (350 mg, 0.56 mM) was added to the solution and stirred until a particle-free solution was achieved. Water for irrigation was added with stirring to achieve a target volume of 100 ml.

Samples of the formulation were analysed in accordance with the methods of Example 1.

EXAMPLE 20

Preparation of a Pharmaceutical Aqueous Solution Formulation Comprising 35 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulfonic acid and 20% w/v 2-hydroxypropyl-beta-cyclodextrin Ethanesulfonic acid (70% w/v) (3144.7 microL, 100 mM) was diluted with water for irrigation (80 ml). 2-Hydroxypropyl-beta-cyclodextrin (93% w/w adjusted potency) (21.57 g, 14.72 mM) was added and the solution was stirred until a particle-free solution was achieved. 1-(4-{[4-(Dimethylamino)piperidin-1-yl]carbonyl}phenyl)-3-[4-(4,6-dimorpholin-4-yl-1,3,5-triazin-2-yl)phenyl]urea (350 mg, 0.56 mM) was added to the solution and stirred until a particle-free solution was achieved. Water for irrigation was added with stirring to achieve target volume of 100 ml.

Samples of the formulation were analysed in accordance with the methods of Example 1.

EXAMPLE 21

Preparation of a Pharmaceutical Aqueous Solution Formulation Comprising 20 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulfonic acid and 20% w/v gamma-cyclodextrin Ethanesulfonic acid (70% w/v) (3144.7 microL, 100 mM) was diluted with water for irrigation (80 ml). Gamma-cyclodextrin (assumed 100% potency) (20 g, 15.4 mM) was added and the solution was stirred until a particle-free solution was achieved. 1-(4-{[4-(Dimethylamino)piperidin-1-yl]carbonyl}phenyl)-3-[4-(4,6-dimorpholin-4-yl-1,3,5-triazin-2-yl)phenyl]urea (200 mg, 0.32 mM) was added to the solution and stirred until a particle-free solution was achieved. Water for irrigation was added with stirring to achieve target volume of 100 ml.

Samples of the formulation were analysed in accordance with the methods of Example 1.

EXAMPLE 22

Preparation of a Pharmaceutical Aqueous Solution Formulation Comprising 30 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea, methanesulfonic acid and 20% w/v sulphobutylether-3-cyclodextrin (SBECD)

Methanesulfonic acid (99% w/w purity) (0.65 ml, 100 mM) was dissolved in water for irrigation (80 ml). Sulphobutylether-3-cyclodextrin (SBECD) (93% w/w adjusted potency) (21.57 g, 9.62 mM) was added and the solution was stirred until a particle free solution was achieved. 1-(4-{[4-(Dimethylamino)piperidin-1-yl]carbonyl}phenyl)-3-[4-(4,6-dimorpholin-4-yl-1,3,5-triazin-2-yl)phenyl]urea (300 mg, 0.48 mM) was added to the solution and stirred until a particle-free solution was achieved. Water for irrigation was added with stirring to achieve a target volume of 100 ml.

Samples of the formulation were analysed in accordance with the methods of Example 1.

EXAMPLE 23

Preparation of a Pharmaceutical Aqueous Solution Formulation Comprising 30 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea, methanesulfonic acid and 20% w/v gamma-cyclodextrin Methanesulfonic acid (99% w/w purity) (0.65 ml, 100 mM) was diluted with water for irrigation (80 ml). Gamma-cyclodextrin (assumed 100% potency) (20 g, 15.42 mM) was added and the solution was stirred until a particle-free solution was achieved. 1-(4-{[4-(Dimethylamino)piperidin-1-yl]carbonyl}phenyl)-3-[4-(4,6-dimorpholin-4-yl-1,3,5-triazin-2-yl)phenyl]urea (300 mg, 0.48 mM) was added to the solution and stirred until a particle-free solution was achieved. Water for irrigation was added with stirring to achieve target volume of 100 ml.

Samples of the formulation were analysed in accordance with the methods of Example 1.

FURTHER EXAMPLES OF THE PREPARATION OF PHARMACEUTICAL AQUEOUS SOLUTION FORMULATIONS COMPRISING 1-(4-{[4-(DIMETHYLAMINO)PIPERIDIN-1-YL]CARBONYL}PHENYL)-3-[4-(4,6-DIMORPHOLIN-4-YL-1,3,5-TRIAZIN-2-YL)PHENYL]UREA, A BETA- OR GAMMA-CYCLODEXTRIN AND METHANESULFONIC OR ETHANESULFONIC ACID

The following, tabulated Examples (indicated by a tick "✓" or cross "x" in the Table) (target volume=100 ml) were prepared in accordance with the method of the relevant Example 19, 20, 21, 22, 23 using the ingredient specification tabulated below.

These Examples were analysed by the visual method defined in European Pharmacopoeia Method 2.9.20 and the OPM method both as described in Example 1. The results are also tabulated below.

In this Table "particle-free" means that the the formulation was visually clear and free of visible crystallites or particulates, and "opalescent" means that the the formulation had an opalescence that is thought to result from the formation of a chromonic liquid crystal phase.

| API mg/ml/API mM | | | 10/16.2 | 15/24.4 | 20/32.5 | 25/40.6 | 30/48.7 | 35/56.9 |
|---|---|---|---|---|---|---|---|---|
| MSA | 100 mM | HPBCD (20% w/v) | ✓ (1) | ✓ (1) | ✓ (1) | ✓ (1) | ✓ (1) | ✓ (1) (EXAMPLE 19) |
| MSA | 100 mM | AlphaCD (20% w/v) | x (3) | x (3) | x (3) | x (3) | x (3) | x (3) |
| MSA | 100 mM | GammaCD (20% w/v) | ✓ (1) | ✓ (1) | ✓ (1) | ✓ (1) | ✓ (1) (EXAMPLE 23) | x (2) |
| MSA | 100 mM | SBECD (20% w/v) | ✓ (1) | ✓ (1) | ✓ (1) | ✓ (1) | ✓ (1) (EXAMPLE 22) | x (2) |
| MSA | 100 mM | HPBCD (20% w/v) | | | | | ✓ (1) | x (2) |
| MSA | 100 mM | HPBCD (25% w/v) | | | | | ✓ (1) | ✓ (1) |
| ESA | 100 mM | SBECD (20% w/v) | ✓ (1) | ✓ (1) | ✓ (1) | ✓ (1) | ✓ (1) | ✓ (1) |
| ESA | 100 mM | HPBCD (20% w/v) | | | | | | ✓ (1) (EXAMPLE 20) |
| ESA | 100 mM | Gamma CD (20% w/v) | | | ✓ (1) (EXAMPLE 21) | x (2) | x (2) | x (2) |

-continued

| API mg/ml/API mM | | | 40/65.0 | 45/73.1 | 50/81.2 | 55/89.3 | 60/97.5 | 65/105.6 |
|---|---|---|---|---|---|---|---|---|
| MSA | 100 mM | HPBCD (20% W/V) | ✓ (1) | ✓ (1) | ✓ (1) | x (2) | | |
| MSA | 100 mM | AlphaCD (20% w/v) | x (3) | x (3) | x (3) | x (3) | x (3) | |
| MSA | 100 mM | GammaCD (20% w/v) | | | | | | |
| MSA | 100 mM | SBECD (20% w/v) | x (2) | | | | | |
| MSA | 100 mM | HPBCD (20% w/v) | x (2) | | | x (3) | x (3) | x (3) |
| MSA | 100 mM | HPBCD (25% w/v) | x (2) | | | x (3) | x (3) | x (3) |
| ESA | 100 mM | SBECD (20% w/v) | x (2) | | | | | |
| ESA | 100 mM | HPBCD (20% w/v) | x (2) | | | | | |
| ESA | 100 mM | Gamma CD (20% w/v) | | | | | | |

Key
MSA = methanesulphonic acid
ESA = ethanesulphonic acid
API = 1-(4-{[4-(dimethylamino)piperidin-1-yl]carbonyl}phenyl)-3-[4-(4,6-dimorpholin- 4-yl-1,3,5-triazin-2-yl)phenyl]urea
HPBCD = 2-hydroxypropyl-beta-cyclodextrin
AlphaCD = alpha-cyclodextrin
SBECD = sulphobutylether-β-cyclodextrin
GammaCD = gamma-cyclodextrin
(1) = particle-free (and non-opalescent). All these Examples studied are free of visible crystallite or particulate matter and meet the required "clear solution" definition as described earlier.
(2) = particulate, opalescent
(3) = particulate suspension

EXAMPLE 24

Preparation of (a) a Pharmaceutical Aqueous Solution Formulation Comprising 20 mg/ml of 1-(4-{[4-(dimethylamino)piperidin-1-yl]carbonyl}phenyl)-3-[4-(4,6-dimorpholin-4-yl-1,3,5-triazin-2-yl)phenyl]urea, methanesulfonic acid and 20% w/v 2-hydroxypropyl-beta-cyclodextrin; and (b) a lyophilised Composition Thereof (a) Methanesulfonic acid (99% w/w purity) (0.336 ml) (35 mM) was dissolved in water for irrigation (80 ml). 2-Hydroxypropyl-beta-cyclodextrin (21.57 g, 14.72 mM) was dissolved in this buffer solution by stirring to achieve total dissolution. 1-(4-{[4-(Dimethylamino)piperidin-1-yl]carbonyl}phenyl)-3-[4-(4,6-dimorpholin-4-yl-1,3,5-triazin-2-yl)phenyl]urea (200 mg, 0.325 mM) was added to the solution and stirred until a particle-free solution was achieved. Water for irrigation was added with stirring to achieve a target volume of 100 ml.

(b) The formulation from (a) was filled into 10 mL vials to a target volume of 3 ml. The vials were partially stoppered (not sealed) with a 20 mm Gray Lyo D777-1 V10-F597W FluroTec Siliconised (trade mark) stopper. The vials were loaded into stainless steel trays and inserted into a LSL1000 (trade mark) freeze dryer. The shelf temperature was set at 25° C. The freeze drying cycle was run using the tabulated method below.

| Condition | Rate/Hold | Temperature (° C.) | Time (Minutes) | Temperature change (° C./minute) | Pressure (mbar) |
|---|---|---|---|---|---|
| Loading | Hold | 25 | n/a | n/a | 1 Atmosphere* |
| Stabilisation | Hold | 25 | 120 | n/a | 1 Atmosphere* |
| Freeze | Rate | −25 | 500 | 0.1 | 1 Atmosphere* |
| | Hold | −25 | 180 | n/a | 1 Atmosphere* |
| | Rate | −40 | 150 | 0.1 | 1 Atmosphere* |
| | Hold | −40 | 150 | n/a | 1 Atmosphere* |
| Evacuation | Hold | −40 | n/a | n/a | 75 mTorr |
| Primary Drying | Rate | −15 | 112 | 0.5 | 75 mTorr |
| | Hold | −15 | 5810 | n/a | 75 mTorr |
| Secondary Drying | Rate | 0 | 150 | 0.1 | 75 mTorr |
| | Hold | 0 | 480 | n/a | 75 mTorr |
| | Rate | 40 | 400 | 0.1 | 75 mTorr |
| | Hold | 40 | 480 | n/a | 75 mTorr |
| | Rate | 25 | 150 | 0.1 | 75 mTorr |
| Stoppering | Hold | 25 | n/a | n/a | 500 Torr |
| Storage | Hold | 25 | n/a | n/a | |

(*760 Torr)

The freeze dryer was back-filled with sterile filtered nitrogen to a set point of 500 Torr (ca. 666 mbar or 66,600 Pascals), and the vials were fully closed using the stoppers. The freeze dryer was then vented to atmospheric pressure using sterile filtered air and the vials were unloaded from the freeze dryer.

Each vial contained the freeze dried (lyophilised) formulation as an off-white solid.

ANALYSIS OF EXAMPLES 1-18

The Examples shown in the following Table were analysed by the visual method defined in European Pharmacopoeia Method 2.9.20 and the OPM method both as described in Example 1. The results are tabulated below.

Further, the formulations of Examples 1, 2 and 6-18 were each lyophilised by the same method used in Examples 3(b) and 4(b) and then each reconstituted by the same method as used in Examples 5A and 5B.

In this Table "particle-free" means that the the formulation was visually clear and free of visible crystallites or particulates, and "opalescent, particle-free" means that the the formulation was free of visible crystallites or particulates but had a solution opalescence that is thought to result from the formation of a chromonic liquid crystal phase. There are Examples shown where the opalescence disappears on reconstitution of the formulation following lyophilisation. All Examples studied are free of visible crystallite or particulate matter and meet the required "clear solution" definition as described earlier.

| Acid | Example | API (mg/ml) | API (mg) | Acid (mM) | mannitol (mg) | Analysis for formulation prepared in Example | Analysis for formulation obtained after reconstitution following lyophilisation |
|---|---|---|---|---|---|---|---|
| MSA | 1 | 22 | 2200 | 100 | 0 | opalescent, particle-free | particle-free |
| | 3(a) | 22 | 2200 | 100 | 2800 | opalescent, particle-free | — |
| | 5A | | | | | — | particle-free |
| | 6 | 8 | 800 | 100 | 4200 | particle-free | particle-free |
| | 7 | 10 | 1000 | 100 | 4000 | particle-free | particle-free |
| | 8 | 13 | 1300 | 100 | 3700 | opalescent, particle-free | particle-free |
| | 9 | 15 | 1500 | 100 | 3500 | opalescent, particle-free | particle-free |
| | 10 | 15 | 1500 | 100 | 0 | opalescent, particle-free | particle-free |
| | 11 | 30 | 3000 | 100 | 2000 | opalescent, particle-free | particle-free |
| | 12 | 30 | 3000 | 100 | 0 | opalescent, particle-free | opalescent, particle-free |
| | 13[1] | 40 | 4000 | 100 | 1000 | opalescent, particle-free | opalescent, particle-free |
| | 14[1] | 40 | 4000 | 100 | 0 | opalescent, particle-free | opalescent, particle-free |
| | 15 | 20 | 2000 | 50 | 3000 | opalescent, particle-free | opalescent, particle-free |
| ESA | 2 | 22 | 2200 | 100 | 0 | opalescent, particle-free | opalescent, particle-free |
| | 4(a) | 22 | 2200 | 100 | 2800 | opalescent, particle-free | — |
| | 5B | | | | | — | opalescent, particle-free |
| | 16 | 30 | 3000 | 100 | 2000 | opalescent, particle-free | opalescent, particle-free |
| | 17 | 20 | 2000 | 50 | 3000 | opalescent, particle-free | particle-free |
| | 18 | 10 | 1000 | 100 | 4000 | particle-free | particle-free |

Footnote

[1] Although this formulation meets the "clear solution" criterion, it is unsuitable for the intended purpose since it is a viscous solution that reconstitutes very slowly Key MSA = methanesulphonic acid ESA = ethanesulphonic acid API = 1-(4-{[4-(dimethylamino)piperidin-1-yl]carbonyl}phenyl)-3-[4-(4,6-dimorpholin-4-yl-1,3,5-triazin-2-yl)phenyl]urea Chemical Stability of a Lyophilised Solid Formulations of the Invention Two Samples of lyophilised formulations of the invention were prepared.

Sample A was prepared by a similar procedure to that of Example 3 except that 2000 mg of 1-(4-{[4-(dimethylamino)piperidin-1-yl]carbonyl}phenyl)-3-[4-(4,6-dimorpholin-4-yl-1,3,5-triazin-2-yl)phenyl]urea (i.e. 20 mg/ml), 100 mM of methanesulfonic acid (0.65 ml) and 3000 mg of mannitol were used to prepare the lyophile.

Sample B was prepared by a similar procedure to that of Example 4 except that 2000 mg of 1-(4-{[4-(dimethylamino)piperidin-1-yl]carbonyl}phenyl)-3-[4-(4,6-dimorpholin-4-yl-1,3,5-triazin-2-yl)phenyl]urea (i.e. 20 mg/ml), 100 mM of ethanesulfonic acid and 3000 mg of mannitol were used to prepare the lyophile.

Separate portions of Samples A and B were each housed in 10 mL clear vials and 20 were stored at 25° C./60% Relative Humidity ("RH"), 40° C./75% RH or 5° C. for 6 weeks.

After 6 weeks storage as above, the Samples were each tested for chemical purity using Ultra High Performance Liquid Chromatography (UHPLC) using the following methodology in order to measure any chemical degradation during the period of testing.

UHPLC Method

The solutions, samples, standards and UHPLC method are as below:

Reference Standard: 1-(4-{[4-(dimethylamino)piperidin-1-yl]carbonyl}phenyl)-3-[4-(4,6-dimorpholin-4-yl-1,3,5-triazin-2-yl)phenyl]urea with a known potency value.

Diluent: Acetonitrile/Water/Trifluoroacetic acid (750:250:1 v/v/v)

Mobile Phase A: Acetonitrile/Water/Trifluoroacetic acid (97:3:1 v/v/v)

Mobile Phase B: Acetonitrile/Trifluoroacetic acid (1000:1 v/v).

(Note: larger or smaller volumes of solutions may be prepared using the appropriate ratio of components)

Standard and Check Standard Preparations:
Accurately prepare two solutions of ca. 0.2 mg/mL (+/− 10%) of 1-(4-{[4-(dimethylamino) piperidin-1-yl]carbonyl}phenyl)-3-[4-(4,6-dimorpholin-4-yl-1,3,5-triazin-2-yl)phenyl]urea Reference Standard in Diluent, and record the concentrations accurately of both. These are the Standard and Check standard preparations.

Sensitivity Solution:
Accurately dilute the Standard preparation to a concentration of approximately 0.1 microgram/ml of 1-(4-{[4-(dimethylamino)piperidin-1-yl]carbonyl}phenyl)-3-[4-(4,6-dimorpholin-4-yl-1,3,5-triazin-2-yl)phenyl]urea using the Diluent.

Sample Preparation:
Reconstitute Sample A or B after storage by adding 3.0 ml of water to each in the 10 ml vial, shake the vial to dissolve the solid and wait for the bubbles to disappear. Transfer 1.0 ml of the solution into a 100 ml volumetric flask. Dilute to the set volume with Diluent.

Chromatographic Conditions:
Liquid chromatographic system—Agilent 1290 Infinity II™ with 380 μl Jet Weaver™
Column: Waters BEH C18™ 15 cm×2.1 mm, 1.7 μm or equivalent
Column Temperature: 20° C.
Injection Volume: 2 μL
Flow Rate: 0.25 mL/min.
Flow Cell: G4212-60008, 10 mm path length, 1.0 μL
Detection: UV at 240 nm/4 nm slit width
Run Time: 77 minutes
Mobile Phase A
Mobile Phase B
Needle wash solution: Water/Acetonitrile (95:5 v/v), multi wash 20 s.
Seal wash solution: Water/Propan-2-ol (90:10 v/v)

Linear Gradient Table:

| Time (minutes) | % Mobile Phase A | % Mobile Phase B |
|---|---|---|
| 0 | 95 | 5 |
| 5.0 | 95 | 5 |
| 31.4 | 78 | 22 |
| 42.3 | 78 | 22 |
| 65.0 | 5 | 95 |
| 67.0 | 5 | 95 |
| 67.1 | 95 | 5 |
| 77.0 | 95 | 5 |

Explanatory Notes

Condition the UHPLC system, prior to starting the analysis, with the mobile phases. Prior to running samples, ensure that the system is suitable for use by injecting blank diluent, sensitivity solution and standard preparation using the chromatographic conditions above.

The following criteria must be satisfied on initial UHPLC set-up or after any significant change to the system. It is recommended to inject at least one conditioning blank prior to testing system suitability.

Figure 3:
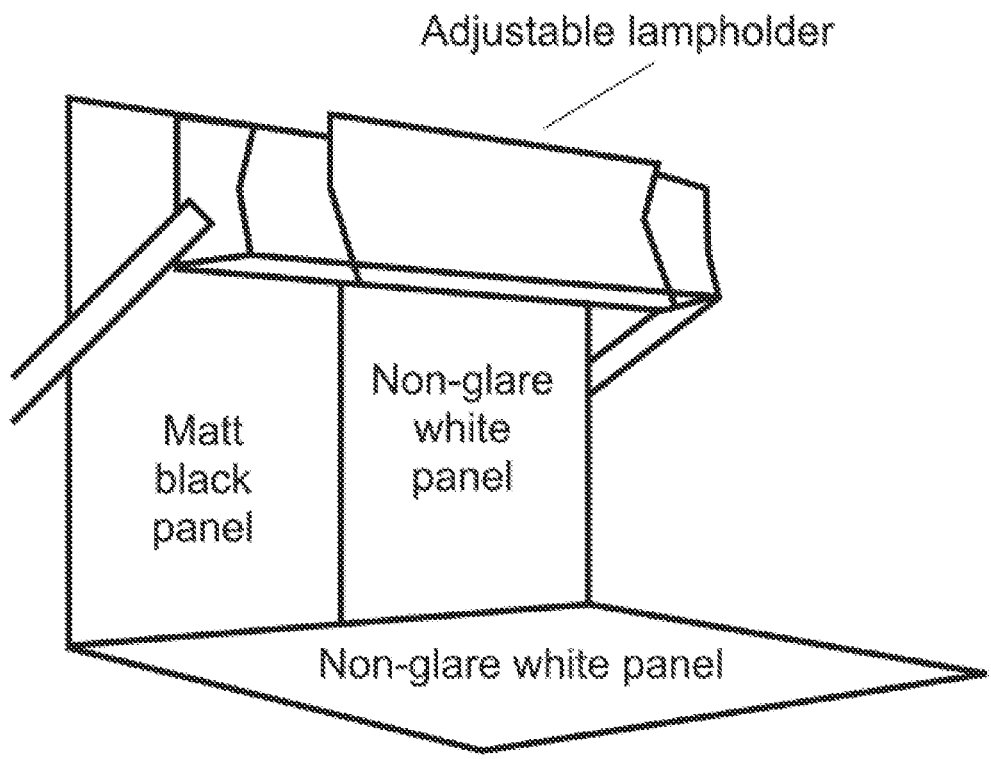

| Test | # of Injections | Solution | Criteria |
|---|---|---|---|
| Blank | 1 | Diluent | Chromatogram similar to FIGS. 3 and 4 |
| Signal to Noise | 1 | Sensitivity Solution | European Pharmacopoeia (EP)/United States Pharmacopoeia (USP) Signal to Noise ≥ 10 |
| Repeatability Retention time | 5 1* | Standard preparation | Relative Standard Deviation ≤ 2.0% 38-44 minutes |
| Efficiency (Plate)** | | | Plate number for 1-(4-{[4-(dimethylamino)piperidin-1-yl]carbonyl}phenyl)-3-[4-(4,6-dimorpholin-4-yl-1,3,5-triazin-2-yl)phenyl]urea peak ≥ 10,000 |
| Peak Asymmetry (T)** | | | 0.9 ≤ T ≤ 2.0 for 1-(4-{[4-(dimethylamino)piperidin-1-yl]carbonyl}phenyl)-3-[4-(4,6-dimorpholin-4-yl-1,3,5-triazin-2-yl)phenyl]urea peak |

-continued

| Test | # of Injections | Solution | Criteria |
|---|---|---|---|
| Resolution | 1 | | Resolution between 1-(4-{[4-(dimethylamino)piperidin-1-yl]carbonyl}phenyl)-3-[4-(4,6-dimorpholin-4-yl-1,3,5-triazin-2-yl)phenyl]urea peak and ((4-(4,6-dimorpholino-1,3,5-triazin-2-yl)phenyl)-l2-azaneyl)((4-(4-(methyl-l2-azaneyl)piperidine-1-carbonyl)phenyl)-l2-azaneyl)methanone ≥ 1.0 |

*Use average of all system suitability (repeatability) injections.
**Refer to United States Pharmacopoeia (USP) calculation equations for Efficiency and Peak Asymmetry.

Inject the check standard preparation according to the chromatographic conditions above. The response factor (calculated from the area, standard weight, dilution factor and purity factor of the standard) of this check standard preparation must be within ±2% of the standard preparation.

After the system suitability has been demonstrated, inject the blank solution, standard preparation and prepared test samples, followed by an injection of the standard preparation, according to the chromatographic conditions above. It is recommended that no more than 6 test samples be injected between standard preparation injections. For each injection (standard and sample), measure the retention time and area of the 1-(4-{[4-(dimethylamino) piperidin-1-yl]carbonyl}phenyl)-3-[4-(4,6-dimorpholin-4-yl-1,3,5-triazin-2-yl)phenyl]urea peak in each chromatogram. For each sample injection, also measure the retention times and peak area of any peaks present in the sample injection that do not appear in the blank injection. Do not integrate gradient artifacts, if present. Compare the blank injection chromatogram to the sample chromatogram to determine which peaks in the sample are related to the blank and gradient artifact peaks. Calculate the % w/w degradants and report the individual degradant peaks which are at or above 0.05% w/w. Unknown degradants should be reported individually by their relative retention time. Known degradants should be reported individually by name.

The results are summarised in the Tables below.

Key

NMT=Not More Than.

RRT=Relative Retention Time

NO=Not Observed

Degradant 1

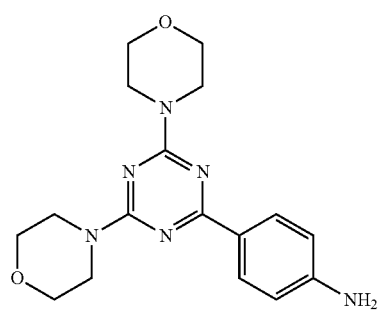 [SMILES: Nc1ccc(-c2nc(N3CCOCC3)nc(N3CCOCC3)n2)cc1]

Degradants 2, 3, 4, 5 and 6

These were each characterised by their RRT only.

Sample A Results

| | 5° C. | 25° C./60% RH | 40° C./75% RH |
|---|---|---|---|
| Degradant 1 | 0.10 | 0.10 | 0.10 |
| Degradant 2 RRT~1.150 | NMT 0.05 | NO | NO |
| Degradant 3 RRT~1.179 | NMT 0.05 | NMT 0.05 | NMT 0.05 |
| Degradant 5 RRT~1.24 | 0.14 | 0.25 | 0.65 |
| Degradant 6 RRT~1.324 | 0.08 | 0.08 | 0.08 |
| Total degradants (w/w) | 0.32 | 0.43 | 0.83 |

Sample B Results

| | 5° C. | 25° C./60% RH | 40° C./75% RH |
|---|---|---|---|
| Degradant 1 | 0.09 | 0.12 | 0.11 |
| Degradant 2 RRT~1.150 | NO | 0.06 | NO |
| Degradant 3 RRT~1.179 | 0.06 | 0.07 | NMT 0.05 |
| Degradant 4 RRT~1.185 | NO | NO | NO |
| Degradant 5 RRT~1.24 | 0.14 | 0.25 | 0.99 |
| Degradant 6 RRT~1.324 | 0.08 | 0.08 | 0.08 |
| Total degradants (w/w) | 0.37 | 0.58 | 1.18 |

CONCLUSION

The results show that Samples A and B are chemically stable for at least 6 weeks at 25° C./60% RH.

The invention claimed is:

1. A pharmaceutical aqueous solution formulation comprising (a) 1-(4-{[4-(dimethylamino)piperidin-1-yl]carbonyl}phenyl)-3-[4-(4,6-dimorpholin-4-yl-1,3,5-triazin-2-yl)phenyl]urea, or a methanesulphonate salt thereof, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 35 mg/ml or up to 30 mg/ml and sufficient methanesulphonic acid is present to provide a clear solution; or (b) 1-(4-{[4-(dimethylamino) piperidin-1-yl]carbonyl}phenyl)-3-[4-(4,6-dimorpholin-4-yl-1,3,5-triazin-2-yl)phenyl]urea, or an ethanesulphonate salt thereof, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of less than 35 mg/ml or up to 30 mg/ml and sufficient ethanesulphonic acid is present to provide a clear solution.

2. A pharmaceutical aqueous solution formulation as claimed in claim 1 comprising (a) 1-(4-{[4-(dimethylamino)piperidin-1-yl]carbonyl}phenyl)-3-[4-(4,6-dimorpholin-4-yl-1,3,5-triazin-2-yl)phenyl]urea, or a methanesulphonate salt thereof, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml and sufficient methanesulphonic acid is present to provide a clear solution; or (b) 1-(4-{[4-(dimethylamino)piperidin-1-yl]carbonyl}phenyl)-3-[4-(4,6-dimorpholin-4-yl-1,3,5-triazin-2-yl)phenyl]urea, or an ethanesulphonate salt thereof, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 30 mg/ml and sufficient ethanesulphonic acid is present to provide a clear solution.

3. A pharmaceutical aqueous solution formulation as claimed in claim 2 comprising 1-(4-{[4-(dimethylamino)piperidin-1-yl]carbonyl}phenyl)-3-[4-(4,6-dimorpholin-4-yl-1,3,5-triazin-2-yl)phenyl]urea, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 22 mg/ml and sufficient methanesulphonic acid is present to provide a clear solution.

4. A pharmaceutical aqueous solution formulation as claimed in claim 2 comprising 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate, methanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 22 mg/ml and sufficient methanesulphonic acid is present to provide a clear solution.

5. A pharmaceutical aqueous solution formulation as claimed in claim 2 comprising 1-(4-{[4-(dimethylamino)piperidin-1-yl]carbonyl}phenyl)-3-[4-(4,6-dimorpholin-4-yl-1,3,5-triazin-2-yl)phenyl]urea, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 22 mg/ml and sufficient ethanesulphonic acid is present to provide a clear solution.

6. A pharmaceutical aqueous solution formulation as claimed in claim 2 comprising 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea is present at a solution concentration of from 6 to 22 mg/ml and sufficient ethanesulphonic acid is present to provide a clear solution.

7. A pharmaceutical aqueous solution formulation as claimed in claim 1 that additionally comprises a pharmaceutically acceptable beta-cyclodextrin or gamma-cyclodextrin.

8. A pharmaceutical aqueous solution formulation as claimed in claim 7 wherein the pharmaceutically acceptable beta-cyclodextrin is hydroxypropyl-beta-cyclodextrin or sulphobutylether-β-cyclodextrin (SBECD), or is a mixture thereof, and the pharmaceutically acceptable gamma-cyclodextrin is gamma-cyclodextrin.

9. A pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate, methanesulphonic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate is present at a solution concentration of less than 55 mg/ml or up to 50 mg/ml and sufficient methanesulphonic acid and 2-hydroxypropyl-beta-cyclodextrin are present to provide a clear solution.

10. A pharmaceutical aqueous solution formulation as claimed in claim 9, wherein 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate is present at a solution concentration of up to 45 mg/ml, up to 40 mg/ml, up to 35 mg/ml, up to 30 mg/ml, from 6 to 50 mg/ml, from 6 to 30 mg/ml, from 8 to 30 mg/ml, from 10 to 35 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient methanesulphonic acid and 2-hydroxypropyl-beta-cyclodextrin are present to provide a clear solution.

11. A pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate, methanesulphonic acid, sulphobutylether-β-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate is present at a solution concentration of less than 35 mg/ml or up to 30 mg/ml and sufficient methanesulphonic acid and sulphobutylether-β-cyclodextrin are present to provide a clear solution.

12. A pharmaceutical aqueous solution formulation as claimed in claim 11, wherein 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate is present at a solution concentration of from 6 to 30 mg/ml, from 8 to 30 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient methanesulphonic acid and sulphobutylether-β-cyclodextrin are present to provide a clear solution.

13. A pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5- triazin-2-yl)phenyl]urea methanesulphonate, methanesulphonic acid, gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate is present at a solution concentration of less than 35 mg/ml or up to 30 mg/ml and sufficient methanesulphonic acid and gamma-cyclodextrin are present to provide a clear solution.

14. A pharmaceutical aqueous solution formulation as claimed in claim 13, wherein 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea methanesulphonate is present at a solution concentration of from from 6 to 30 mg/ml, from 8 to 30 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient methanesulphonic acid and gamma-cyclodextrin are present to provide a clear solution.

15. A pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid, 2-hydroxypropyl-beta-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate is present at a solution concentration of less than 40 mg/ml or up to 35 mg/ml and sufficient ethanesulphonic acid and 2-hydroxypropyl-beta-cyclodextrin are present to provide a clear solution.

16. A pharmaceutical aqueous solution formulation as claimed in claim 15, wherein 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate is present at a solution concentration of up to 30 mg/ml, from 6 to 30 mg/ml, from 8 to 30 mg/ml, from 10 to 35 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient ethanesulphonic acid and 2-hydroxypropyl-beta-cyclodextrin are present to provide a clear solution.

17. A pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid, sulphobutylether-β-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate is present at a solution concentration of less than 40 mg/ml or up to 35 mg/ml and sufficient ethanesulphonic acid and sulphobutylether-β-cyclodextrin are present to provide a clear solution.

18. A pharmaceutical aqueous solution formulation as claimed in claim 17, wherein 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate is present at a solution concentration of up to 30 mg/ml, from 6 to 30 mg/ml, from 8 to 30 mg/ml, from 10 to 30 mg/ml, from 8 to 22 mg/ml, from 10 to 22 mg/ml, from 15 to 22 mg/ml, from 10 to 20 mg/ml, from 6 to 25 mg/ml or from 10 to 25 mg/ml and sufficient ethanesulphonic acid and sulphobutylether-β-cyclodextrin are present to provide a clear solution.

19. A pharmaceutical aqueous solution formulation comprising 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate, ethanesulphonic acid, gamma-cyclodextrin and water, wherein 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate is present at a solution concentration of less than 25 mg/ml or up to 20 mg/ml and sufficient ethanesulphonic acid and gamma-cyclodextrin are present to provide a clear solution.

20. A pharmaceutical aqueous solution formulation as claimed in claim 19, wherein 1-(4-{[4-(dimethylamino)piperidin-1-yl]carbonyl}phenyl)-3-[4-(4,6-dimorpholin-4-yl-1,3,5-triazin-2-yl)phenyl]urea or 1-(4-{[4-(dimethylamino)piperidin-1-yl]carbonyl}phenyl)-3-[4-(4,6-dimorpholin-4-yl-1,3,5-triazin-2-yl)phenyl]urea ethanesulphonate is present at a solution concentration of from 6 to 20 mg/ml, from 8 to 20 mg/ml, from 10 to 20 mg/ml, from 8 to 15 mg/ml, or from 15 to 20 mg/ml and sufficient ethanesulphonic acid and gamma-cyclodextrin are present to provide a clear solution.

21. A formulation as claimed in claim 1, wherein from 10 to 200 mM, 20 to 200 mM, 30 to 200 mM or from 50 to 200 mM of methanesulphonic acid or ethanesulphonic acid, as appropriate, is used.

22. A formulation as claimed in claim 7, wherein from 2 to 30% w/v, 3 to 20% w/v, from 5 to 20% w/v or from 15 to 30% w/v of the cyclodextrin is used.

23. A lyophilized formulation obtainable by freeze drying a formulation as claimed in claim 1.

24. A lyophilized formulation as claimed in claim 23 comprising mannitol as a bulking agent.

25. A pharmaceutical aqueous solution formulation obtainable as a clear solution by reconstitution or constitution of a lyophilized formulation as claimed in claim 23 using water or an aqueous solution comprising a tonicity modifier.

26. A pharmaceutical aqueous solution formulation as claimed in claim 25 wherein the tonicity modifier is dextrose, sucrose or mannitol, or is a mixture of any 2 or more thereof.

27. A pharmaceutical aqueous solution formulation as claimed in claim 1, that is adjusted, as necessary, to have a pH suitable for intravenous or parenteral administration.

28. A formulation as claimed in claim 1 for use as a medicament.

29. A formulation as claimed in claim 1 for use in the treatment of breast cancer, ovarian cancer, endometrial cancer, colorectal cancer, renal cancer, glioblastoma, lung cancer or prostate cancer.

30. A method of treatment of cancer in a mammal comprising treatment of the mammal with an effective amount of a formulation as claimed in claim 1, wherein the cancer is breast cancer, ovarian cancer, endometrial cancer, colorectal cancer, renal cancer, glioblastoma, lung cancer or prostate cancer.

\* \* \* \* \*